(12) United States Patent
Zamuruyev

(10) Patent No.: US 12,023,527 B2
(45) Date of Patent: Jul. 2, 2024

(54) METHODS AND APPARATUS FOR PERSONAL PROTECTIVE RESPIRATORY DEVICE

(71) Applicant: EcoBuilders, Co., Camden, DE (US)

(72) Inventor: Konstantin Zamuruyev, Sierra Madre, CA (US)

(73) Assignee: EcoBuilders, Co., Camden, DE (US)

( * ) Notice: Subject to any disclaimer, the term of this patent is extended or adjusted under 35 U.S.C. 154(b) by 449 days.

(21) Appl. No.: 17/341,996

(22) Filed: Jun. 8, 2021

(65) Prior Publication Data

US 2021/0378323 A1    Dec. 9, 2021

Related U.S. Application Data

(60) Provisional application No. 63/035,969, filed on Jun. 8, 2020.

(51) Int. Cl.

| | |
|---|---|
| A62B 18/02 | (2006.01) |
| A41D 13/11 | (2006.01) |
| A61L 9/20 | (2006.01) |
| A62B 18/04 | (2006.01) |
| A62B 18/08 | (2006.01) |

(Continued)

(52) U.S. Cl.
CPC ............. *A62B 18/02* (2013.01); *A41D 13/11* (2013.01); *A61L 9/20* (2013.01); *A62B 18/045* (2013.01); *A62B 18/084* (2013.01); *A62B 23/025* (2013.01); *B01D 39/08* (2013.01)

(58) Field of Classification Search
CPC .... A62B 7/00; A62B 7/10; A62B 9/00; A62B 9/04; A62B 18/00; A62B 18/003; A62B 18/006; A62B 18/02; A62B 18/04; A62B 18/045; A62B 18/08; A62B 18/082; A62B 18/084; A62B 17/00; A62B 17/04; A62B 19/00; A62B 23/00; A61L 9/18; A61L 9/20; A61L 9/205; A61L 9/22; A61L 2209/133; A61L 2209/134; A61L 2209/212; A41D 13/11; A41D 13/1153; A41D 13/12;

(Continued)

(56) References Cited

U.S. PATENT DOCUMENTS

2021/0290989 A1* 9/2021 Hall ................. A62B 17/003
2021/0330831 A1* 10/2021 Laty ................. A62B 9/006

(Continued)

FOREIGN PATENT DOCUMENTS

WO    WO-2021222410 A1 * 11/2021

*Primary Examiner* — Colin W Stuart
(74) *Attorney, Agent, or Firm* — Noblitt & Newson, PLLC

(57) ABSTRACT

An apparatus for a personal protective respiratory device according to various aspects of the present technology include a wearable housing having air filtration system and an air sterilizing system for providing filtered and sterilized airflow to a user. One or more internal fans generate a mass flow rate of air through the duct system. Filtered and sterilized air exits the housing above the user's forehead and is directed onto a face shield to create an elevated pressure zone of air in the region around the user's face. Both dispelled air from the housing and exhaled air from the user flow downwardly along an inner surface of the face shield and away from the user. The face shield may include an edge filter to capture respiratory droplets. A head gown may be coupled to the housing and head shield to provide additional protection against respiratory droplets.

24 Claims, 12 Drawing Sheets

(51) Int. Cl.
*A62B 23/02* (2006.01)
*B01D 39/08* (2006.01)

(58) Field of Classification Search
CPC ...... A41D 13/1218; A42B 3/22; A42B 3/221; A61F 9/06
See application file for complete search history.

(56) References Cited

U.S. PATENT DOCUMENTS

| | | | |
|---|---|---|---|
| 2021/0339061 A1* | 11/2021 | Fajardo | A62B 18/08 |
| 2021/0353969 A1* | 11/2021 | Leschinsky | A62B 9/00 |
| 2021/0378346 A1* | 12/2021 | Abghari | A61F 9/045 |
| 2021/0401086 A1* | 12/2021 | Chandler | A41D 13/1161 |
| 2022/0118290 A1* | 4/2022 | Delgatty | A62B 18/02 |
| 2022/0183417 A1* | 6/2022 | Hajianpour | A41D 13/1184 |
| 2022/0257822 A1* | 8/2022 | Nasui | B03C 3/38 |
| 2022/0295935 A1* | 9/2022 | Hall | G02B 27/017 |
| 2022/0331619 A1* | 10/2022 | Joseph | A62B 7/10 |
| 2023/0191169 A1* | 6/2023 | Mestemacher | A62B 18/08 128/858 |

* cited by examiner

METHODS AND APPARATUS FOR PERSONAL PROTECTIVE RESPIRATORY DEVICE

CROSS REFERENCES TO RELATED APPLICATIONS

This application claims the benefit of U.S. Provisional Patent Application No. 63/035,969, filed Jun. 8, 2020, and incorporates the disclosure of the application by reference.

BACKGROUND OF THE TECHNOLOGY

Personal protection equipment (PPE) includes various types of devices directed towards protecting an individual from a selected hazard. One of the more common types of PPE devices is a respiratory filtering device, such as a mask. Most respiratory protective equipment is based on the mechanical filtration of air through a porous media or membrane. The thickness and the pore size of these membrane filters allow filtering of up to 99% of submicron sized particulates. Porous barrier type filters are rated for their ability to retain particulates only. Notably, viruses can be transmitted on particulates significantly smaller than the filtering capability of the porous media, thus compromising the protection of a user. The unfiltered portion of particulates can still transfer a significant number of viruses on their surface. Because products of respiration or air contaminants originating from other sources may contain or carry on their surfaces various bacteria and viruses that are harmful to respiratory organs or other organs of the body, it is beneficial for personal respiratory devices to include a level of sterilization capability.

Another aspect of conventional respiratory PPE devices, such as masks, is that they often rely on a seal between the mask and the user to provide protection. The seal between the face and the mask, however, may be compromised by various factors such as the existence of facial hair, skull shape, or physical activity (e.g. speaking, breathing, and moving). A compromised seal that allows air to pass to the user without being filtered reduces the effectiveness of the mask putting the user at risk.

Another factor which may limit the effectiveness of current respiratory PPE devices is the accumulated bacterial contamination and growth in the mask membrane material itself. For example, during use the material of the filtering element commonly used in face masks is in close proximity to the nose, mouth, and eyes of the user. After a period of use, the membrane filtering material may accumulate a significant number of particles, bacteria, and viruses on its surface. The warmth and humidity of breath may proliferate the growth of bacteria on the filtering material itself, creating a "bacterial sponge" effect. If this occurs, any contact or touching of the mask or repeated use of a used mask may be harmful to the user.

SUMMARY OF THE TECHNOLOGY

An apparatus for a personal protective respiratory device according to various aspects of the present technology include a wearable housing having air filtration system and an air sterilizing system for providing filtered and sterilized airflow to a user. One or more internal fans generate a mass flow rate of air through the duct system. Filtered and sterilized air exits the housing above the user's forehead and is directed onto a face shield to create an elevated pressure zone of air in the region around the user's face. Both dispelled air from the housing and exhaled air from the user flow downwardly along an inner surface of the face shield and away from the user. The face shield may include an edge filter to capture respiratory droplets. A head gown may be coupled to the housing and the head shield to provide additional protection against respiratory droplets.

BRIEF DESCRIPTION OF THE DRAWINGS

A more complete understanding of the present technology may be derived by referring to the detailed description and claims when considered in connection with the following illustrative figures. In the following figures, like reference numbers refer to similar elements and steps throughout the figures.

Elements and steps in the figures are illustrated for simplicity and clarity and have not necessarily been rendered according to any particular sequence. For example, steps that may be performed concurrently or in a different order are illustrated in the figures to help to improve understanding of embodiments of the present technology.

DETAILED DESCRIPTION OF EXEMPLARY EMBODIMENTS

The present technology may be described in terms of functional block components and various processing steps. Such functional blocks may be realized by any number of components configured to perform the specified functions and achieve the various results. For example, the present technology may employ various materials, finishes, dimensions, and geometries, which may carry out a variety of operations suited to a specified application or environment. In addition, the present technology may be practiced in conjunction with any number of systems configured for operation with personal protective breathing devices, air filtering systems, sterilizing systems, and the system described is merely one exemplary application for the technology. Further, the present technology may employ any number of conventional techniques for air filtration, forced airflow, and methods of sterilization.

Methods and apparatus for a personal protective respiratory device according to various aspects of the present technology may operate in conjunction with any type of personal breathing device or filtration technology. Various representative implementations of the present technology may be applied to personal protective equipment (PPE). For example, the described technology may be used to provide a wearer with a continuous supply of filtered and sterilized air while also reducing a likelihood that airborne particulates may come into contact with the wearer's eyes, nose, and mouth.

Figure 1:
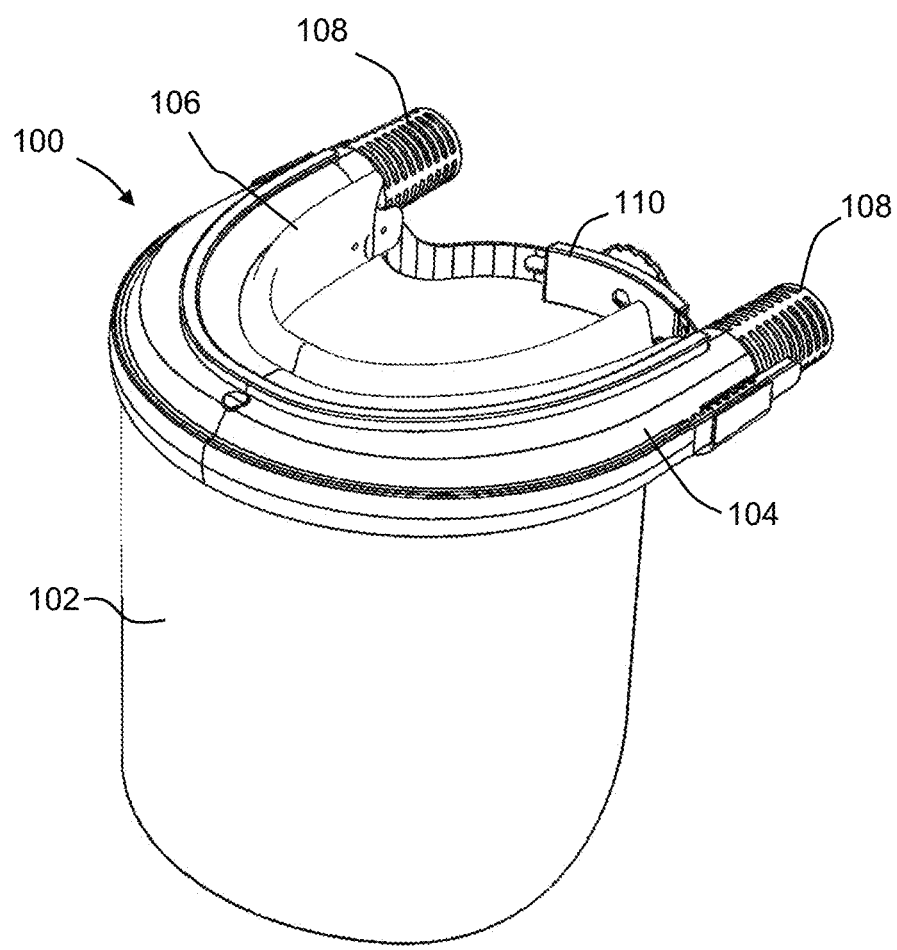
FIG. 1 representatively illustrates a left front perspective view of a personal respiratory device in accordance with an exemplary embodiment of the present technology.
Figure 2A:
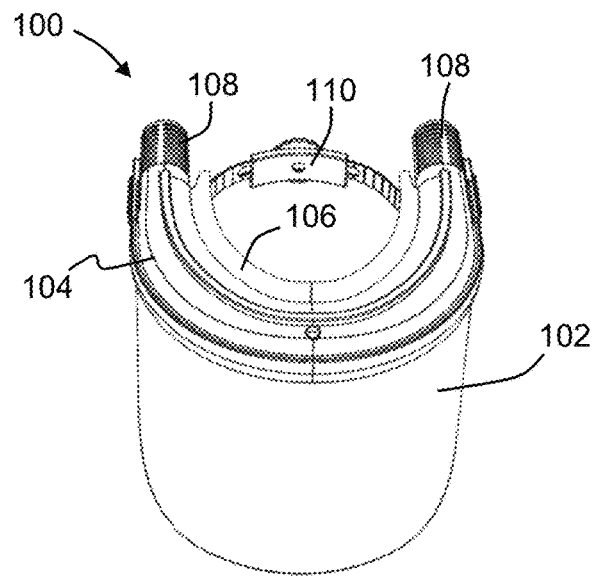
FIG. 2A representatively illustrates an upper front perspective view of the personal respiratory device shown in FIG. 1.
Figure 2B:
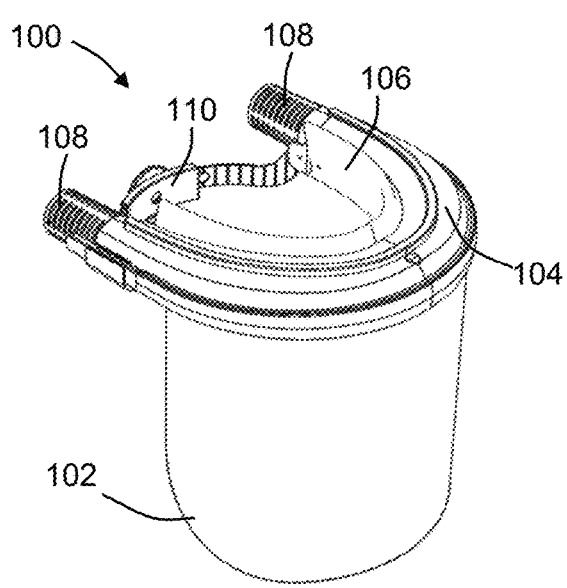
FIG. 2B representatively illustrates a right front perspective view of the personal respiratory device shown in FIG. 1.
Figure 2C:
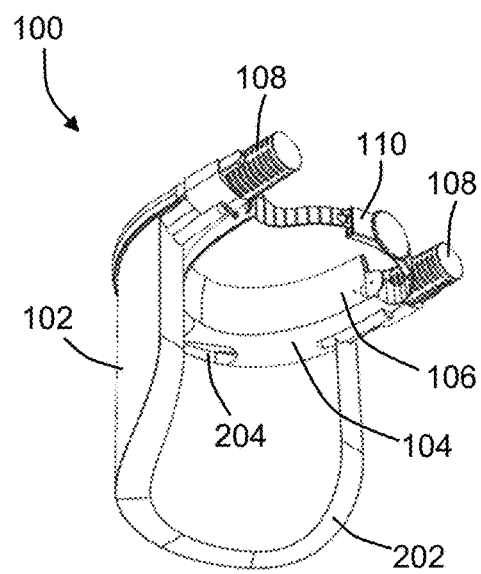
FIG. 2C representatively illustrates a lower perspective view of the personal respiratory device shown in FIG. 1 with an edge filtration device shown on a face shield in accordance with an exemplary embodiment of the present technology.
Figure 2D:
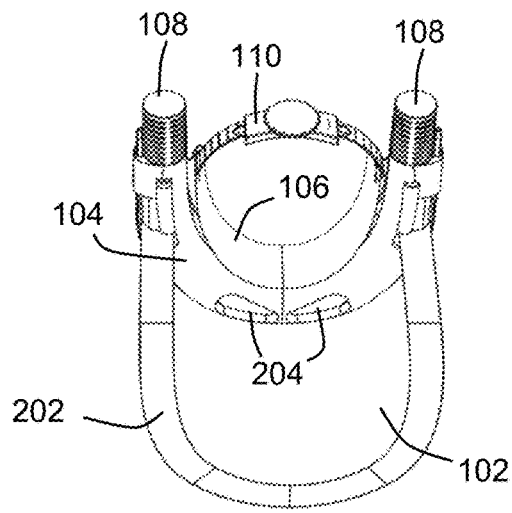
FIG. 2D representatively illustrates a lower rear perspective view of the personal respiratory device shown in FIG. 1 with an edge filtration device shown on a face shield in accordance with an exemplary embodiment of the present technology.
Figure 3A:
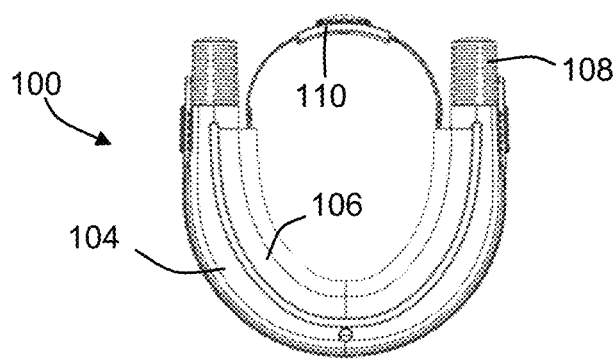
FIG. 3A representatively illustrates a top view of the personal respiratory device shown in FIG. 1 in accordance with an exemplary embodiment of the present technology.
Figure 3B:
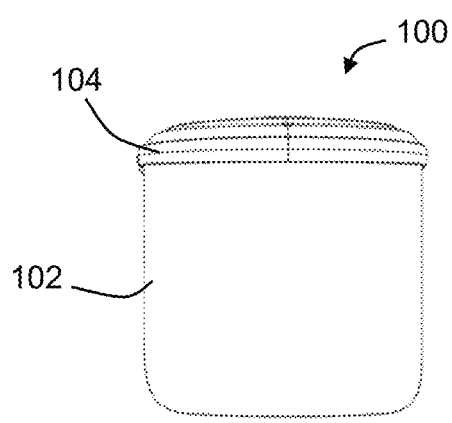
FIG. 3B representatively illustrates a front view of the personal respiratory device shown in FIG. 1 in accordance with an exemplary embodiment of the present technology.
Figure 3C:
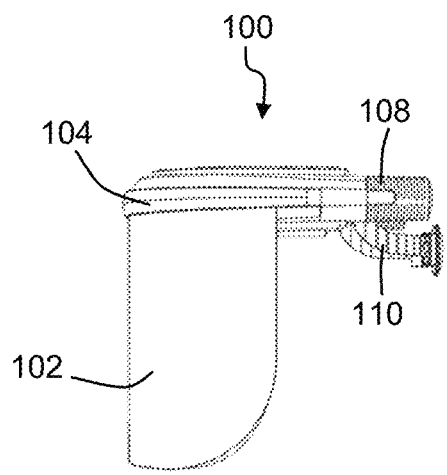
FIG. 3C representatively illustrates a side view of the personal respiratory device shown in FIG. 1 in accordance with an exemplary embodiment of the present technology.
Figure 3D:
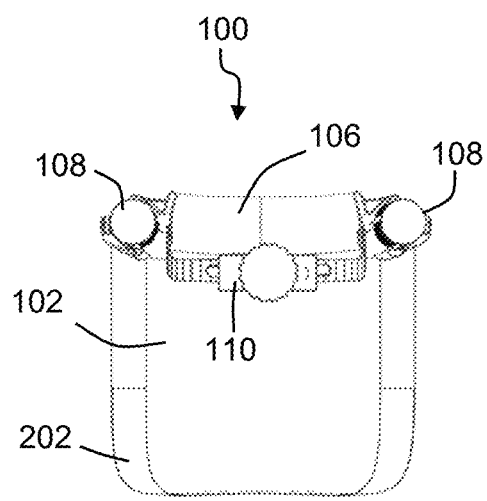
FIG. 3D representatively illustrates a rear view of the personal respiratory device shown in FIG. 1 in accordance with an exemplary embodiment of the present technology.
Figure 3E:
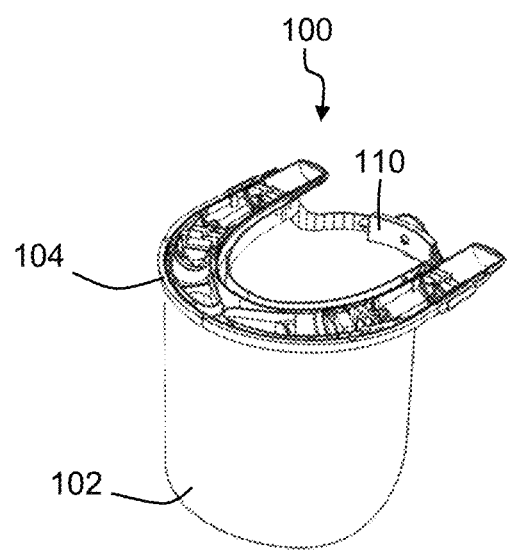
FIG. 3E representatively illustrates a front perspective sectioned view of the personal respiratory device shown in FIG. 1 in accordance with an exemplary embodiment of the present technology.

Referring to FIGS. 1-2D, a personal protective respiratory device 100 may be configured to be worn on a user's head and generally comprise a wearable device having a face shield 102 extending downwardly from a housing 104. A head cushion 106 may be coupled to the housing 104 and be configured to allow the personal protective respiratory device 100 to be fitted on the user's head. An adjustment mechanism 110 may allow the head cushion 106 to be adjusted to better fit a given user's head. The housing 104 may contain an air filtration system 108, an air circulation system (not shown), an air sterilization system (not shown), and an electronic control board (not shown). The housing 104 may also be configured with additional elements, such as: audio and video communication devices; wireless communication system (e.g. to connect to a phone or other remote device); a projection system to display information onto the face shield 102 in a region visible to the user; gas sensors; body temperature monitors; and other sensors, including sensors for heartbeat, blood oxygen level, and sodium level for dehydration.

With additional reference now to FIGS. 3A-3E, and 4, in one embodiment, the housing 104 may generally comprise a u-shaped body having two opposing side sections that extend between a curved forward center section and two rear facing ends configured to be located towards the back of the user's head during use. The curved forward center section is positioned proximate to the user's forehead during use.

The two ends are configured to act as air inlets for an air duct located within the housing 104. The air duct is used to help direct airflow from the two ends towards a set of air outlets 204 positioned proximate to the curved forward center section of the housing 104. The two ends may be integrated with the air filtration system 108 to filter the incoming air.

The housing 104 may comprise any suitable device for containing the working components, providing a pathway for airflow, and for connecting to the face shield 102 and the head cushion 106. For example, the housing 104 may comprise any type of body, housing, helmet having an internal volume for containing various systems and devices such as: the air filtration system 108; a pair of air fans 418; a single, dual, or multi-chambered air duct system; an air sterilization system 414; and an electronic control system 424. In one embodiment, the housing 104 may comprise an upper cover 402 and a lower cover 404 configured to be coupled together to form the internal volume. The upper and lower covers 402, 404 may be coupled together by any suitable method such as: a set of male/female connectors; snap connectors; mechanical fasteners; or the like. The upper and lower covers 402, 404 may be configured to be permanently connected together or they may be configured to be taken apart.

Referring now to FIGS. 4-7, the head cushion 106 allows a user to position the personal protective respiratory device 100 onto their head for use. The head cushion 106 may comprise any suitable device or system for allowing the personal protective respiratory device 100 to be worn such as: a head band or strap; an adjustable mounting harness; a set of compressible foam pads; or the like. In one embodiment, the head cushion 106 may comprise a flexible head strap having a curved center section and two opposing side sections that roughly conform to the u-shape of the housing 104, although one of skill in the art will recognize that the head cushion may comprise any suitable shape capable of being fit to a user's head such as circular, oval, or the like. The flexible head strap may comprise a soft and flexible material such as: neoprene; silicon; rubber; or other soft flexible polymer.

The head cushion 106 may be adjustable to fit a variety of differently sized and shaped heads. For example, the head cushion 106 may comprise an adjustment mechanism 110 extending between the opposing side sections of the head cushion 106 configured to selectively increase or decrease the diameter of the head cushion 106. The adjustment mechanism 110 may comprise any suitable device configured to change the diameter of the head cushion 106 such as: a hook and fastener; a snap back closure; a buckle and strap; or a mechanical ratcheting adjuster. In one embodiment, the adjustment mechanism 110 may comprise an adjustable rotary ratchet 502 configured to increase or decrease the size to fit a given user's head circumference in response to the rotation of knob.

Figure 6:
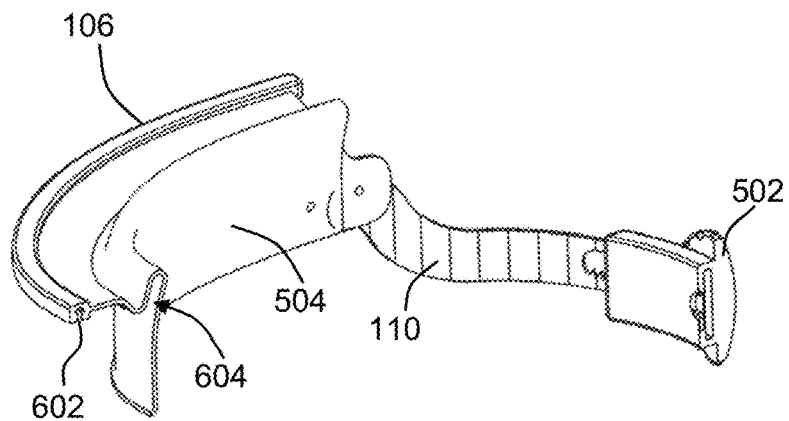
FIG. 6 representatively illustrates a side cutaway view of the head cushion shown in FIG. 5 in accordance with an exemplary embodiment of the present technology.
Figure 7:
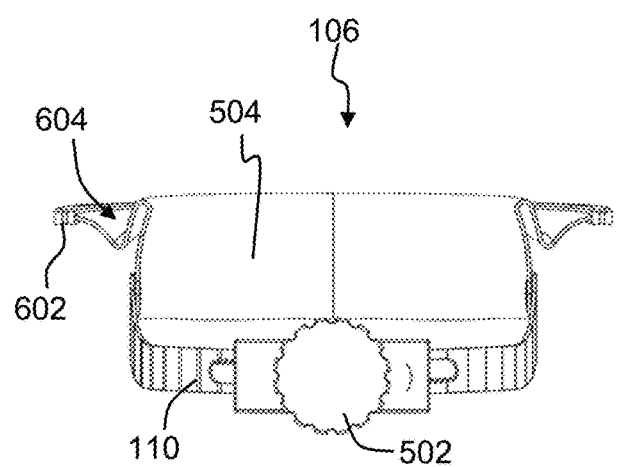
FIG. 7 representatively illustrates a rear cutaway view of the head cushion shown in FIG. 5 in accordance with an exemplary embodiment of the present technology.

The head cushion 106 may also be configured to reduce a transfer of vibrational energy from the housing 104 to the user. For example, the head cushion 106 may comprise a specific shape selected to attenuate vibrations. In combination with the material of the head cushion 106, the transfer of vibrational energy created by internal moving components within the housing 104 to the user may be reduced. With particular reference now to FIGS. 6 and 7, in one embodiment, the head cushion 106 may comprise a double bend profile 604 configured to compress or expand in response to a shape of the user's head. The head cushion 106 may also compress or expand in response to any adjustments made to the adjustment mechanism 110.

The double bend profile 604 acts to suspend the housing 104 around the user's head without providing any direct contact between the housing 104 and the user's head. The double bend profile 604 also absorbs vibrations and reducing the amount of vibration energy felt by the user during operation increasing comfort and reducing fatigue. For example, the geometrical shape and density of the material used to form the head cushion 106 and the double bend profile 604 may also act as a damper for attenuation of mechanical or sound vibrations from the housing 104 adding to the reduction of the transmission of vibrations from the housing 104 to the user's head.

A curvature of the double bend profile 604 may vary around the periphery of the head cushion 106. For example, the double bend profile 604 may have a first shape at a forward center portion of the head cushion 106, wherein the two major curving sections have a first curvature profile. The curvature profile of the major curving sections may change as the head cushion 106 extends rearwardly such that the major curving sections have a second curvature profile along side portions of the head cushion 106. The change in curvature profile around the periphery of the head cushion 106 helps make the head cushion 106 conform and fit comfortably on various sizes and shapes of user heads.

If the head cushion 106 fits better around a user's head, then the head cushion 106 itself may form a seal around the user's head and help prevent ambient air from migrating downwardly into a region between the user's face and the face shield 102 during use. The seal created around the user's head may also prevent treated air from leaking outwardly from the region where the head cushion 106 is in contact with the user's head.

Ergonomic features of the head cushion 106 may be used to further enhance size and shape adjustability and comfort of fit over different head shapes and sizes. For example, an inner surface 504 of the head cushion 106 may be configured to reduce pressure points on the user's head during use. Another example is the inclusion of a groove pattern along the inner surface 504 to improve the ability of the head cushion 106 to remain in a fixed location during use.

Figure 4:
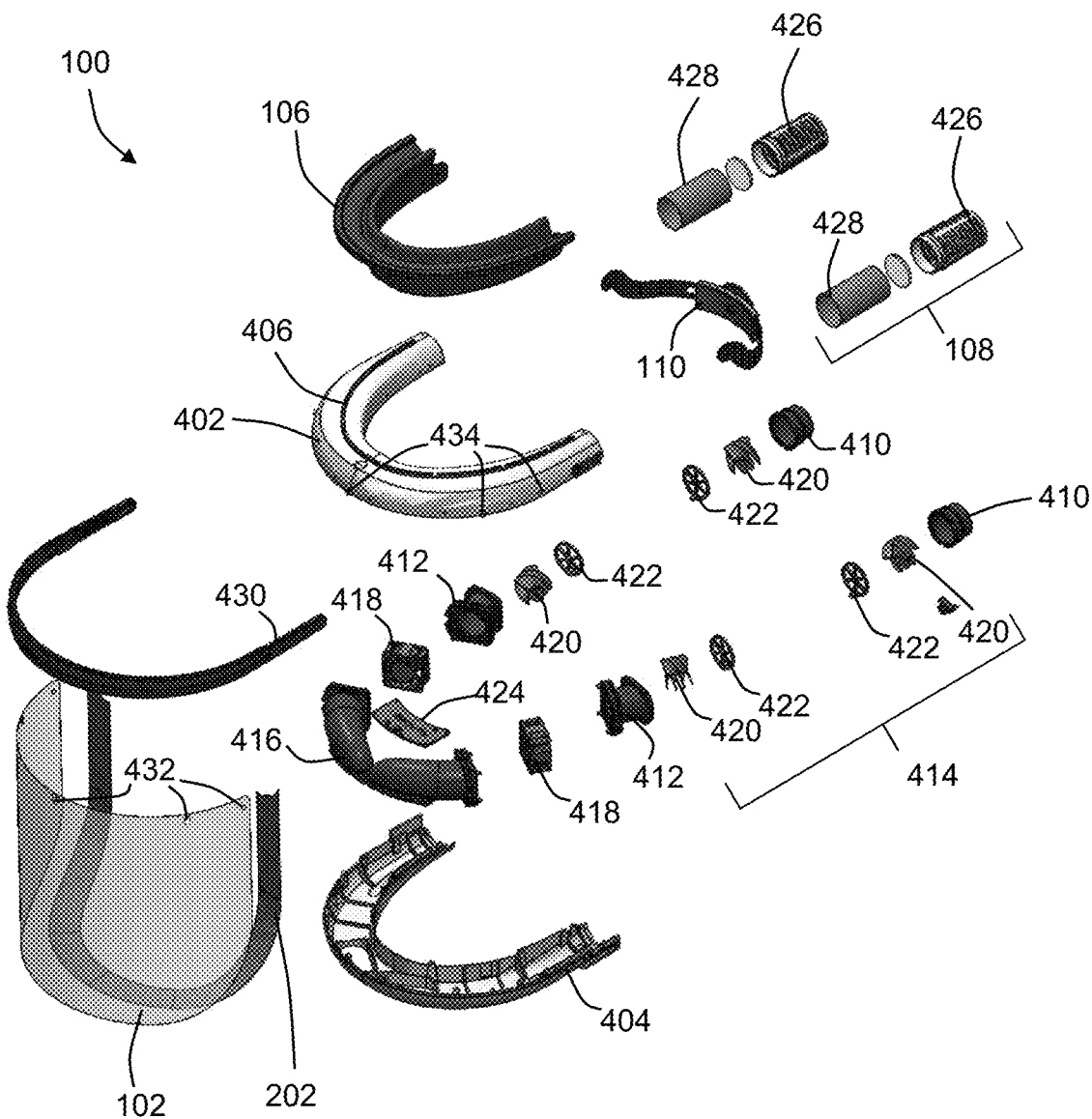
FIG. 4 representatively illustrates an exploded view of the personal respiratory device in accordance with an exemplary embodiment of the present technology.
Figure 5:
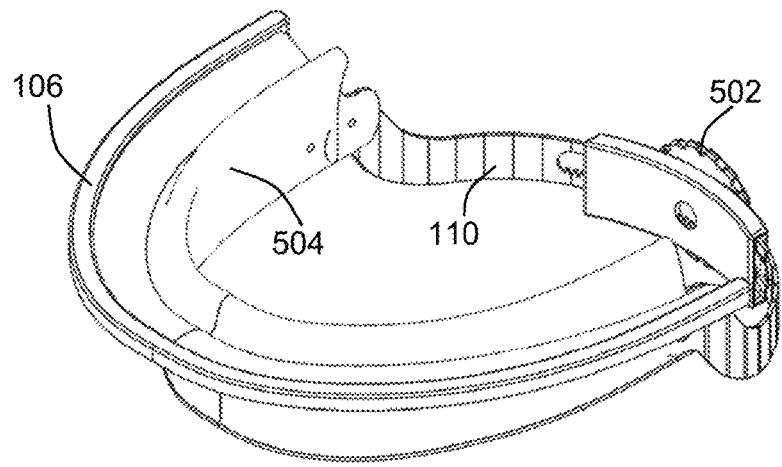
FIG. 5 representatively illustrates a perspective view of a head cushion in accordance with an exemplary embodiment of the present technology.

The head cushion 106 may be coupled to the housing 104 by any suitable method. The head cushion 106 may be permanently attached to the housing 104 or it may be configured to be removable. Referring now to FIGS. 4, 6, and 7, in one embodiment, the head cushion 106 may comprise a receiving cavity 602 that extends around an outer perimeter of the head cushion 106 and is configured to be coupled to a mating male connector 406 disposed along an upper surface of the upper cover 402. The receiving cavity 602 may be configured of the same material as the rest of the head cushion 106 to help attenuate any vibration from the housing 104 through to the head cushion 106.

In an alternative embodiment, the head cushion 106 may be coupled to the housing by a set of mechanical fasteners. A vibration dampening system may be incorporated into the mechanical fasteners to help reduce the transmission of vibration energy from the housing 104 to the head cushion 106. In yet another embodiment, the head cushion 106 may be coupled directly to the housing 104 without the use of any vibration dampening materials and any attenuation of vibration may be achieved by the remainder of the head cushion 106.

The air filtration system 108 is used to filter incoming air and may comprise any type of filtration system for restricting air particulates from entering into the duct system. For example, referring now to FIGS. 1, 2A-2D, 3A, 3B, 3D, 4, and 8, in one embodiment the air filtration system 108 may comprise a pair of filtering elements 428. A single filtering element 428 may be located at each end of side section of the housing 104 and may filter incoming air to a specified level. For example, each filtering element 428 may comprise a replaceable filtration media configured to be positioned within a filter housing 426. The filter housing 426 may be configured to be selectively coupled to the end of the housing 104 to allow a user to replace the filtering elements 428 when necessary. The filtration media may comprise any suitable device or material for filtering particles from air and may be selected according to a desired filtration level. For example, in one embodiment, the filtration media may comprise a mechanical air filter, such as a HEPA filter. The thickness and pore size of each filtering element 428 can be selected based on suitable criteria or application. For example, users can easily change filtering elements 428 depending on the application, ambient air quality, exposure risk, and required protection level.

Each filtering element 428 may comprise a cylindrical shape that can be dropped or otherwise inserted into an accepting circular cavity within the filter housing 426. The filtering element 428 may be secured in place with an outer cage clamp. The cage clamp may be coupled to or otherwise locked into place on the housing 104 with a rotary movement. Conical geometries between the housing 104 and the cage clamp may create an airtight seal for the filter elements 428.

The filtering elements 428 may be formed from any suitable material into a cylindrical shape or any other, shape that can be inserted into the filter housing 426. For example, the filtering elements 428 may be constructed from a flat piece of filtration media arranged into a cylindrical shape. A surface of the filtering elements 428 may be pleated to increase a surface area of the filter elements 428 to reduce the pressure drop through the filtration media.

The surface area of each filtering element 428 may comprise any suitable figure that can achieve a desired specified or flow rate of air for a given pressure drop. For example, a larger surface area will allow a smaller pressure drop at higher flow rates. In one embodiment the surface area of each filtering element 428 may comprise between about 77 $cm^2$ to about 155 $cm^2$. Within this range, measured flow rates of air through the duct system may be between about 75 liters per minute and about 110 liters per minute.

Ambient air is pulled through the air filtration system 108 by the air circulation system. The air circulation system may comprise any suitable system or device for generating a flow rate of air from the inlets through the duct system, to the set of air outlets 204. In various embodiment, the air circulation system may comprise devices such as: propeller style fans, ducted fans, jets, directed air ionization systems, and the like. The air circulation system is configured to generate a sufficient mass flow rate of air at the specified pressure drop at a noise level that is not uncomfortable to the user.

Referring now to FIGS. 4, 8, 9, 17, and 18, in one embodiment, the air circulation system may comprise a pair of frictionless air fans 418 installed downstream of the air filtration system 108 that are configured to establish sufficient pressure drop through the porous filtering membranes to provide airflow at the required flow rate. The air circulation system may be located immediately downstream from the air filtration system 108 or it may be located further downstream from additional working components.

The fans 418 may be powered by a power supply located within the interior of the housing 104, along an external surface of the housing 104, or from an external power source through a wired connection. The fans 418 may include a motor mounting bracket configured with vibration damping material inserts or geometries to reduce vibrations from the motor to the housing 104 to help aid in a user's comfort. The motor mounting bracket may comprise one or more heat exchange elements configured to assist with heat dissipation from the motor. For example, at least a portion of the motor mounting bracket may comprise a thermally conductive material configured to absorb heat from the motor and dissipate it into the airflow, the housing 104, or some other heatsink.

Referring now to FIG. 4 the air sterilization system 414 sterilizes the incoming filtered air from the air filtration system 108 before the airflow passes out of the set of air outlets 204. The air sterilization system 414 may comprise any system or device for sterilizing, or otherwise killing or deactivating bacteria, viruses, and/or other microbial organisms in a passing mass flow of air.

The air sterilization system 414 is configured to control an exposure dose at a specified wavelength of ultraviolet (UV) light to disrupt bacterial and viral content transmitted on the surface of particulates that are smaller than the filtering capability of the air filtration system 108. The residency time of the air in the air sterilization system 414 and a power of the UV light source may be adjusted to generate an exposure dose to deactivate most respiratory viruses of between about 2 mJ to about 4 mJ at approximately 265 nm. The exposure dose may comprise any other suitable figure determined according to any desired criteria such as a targeted type of virus or bacteria, mass flow rate of air, size of internal ducting, or any other suitable factor.

Figure 8:
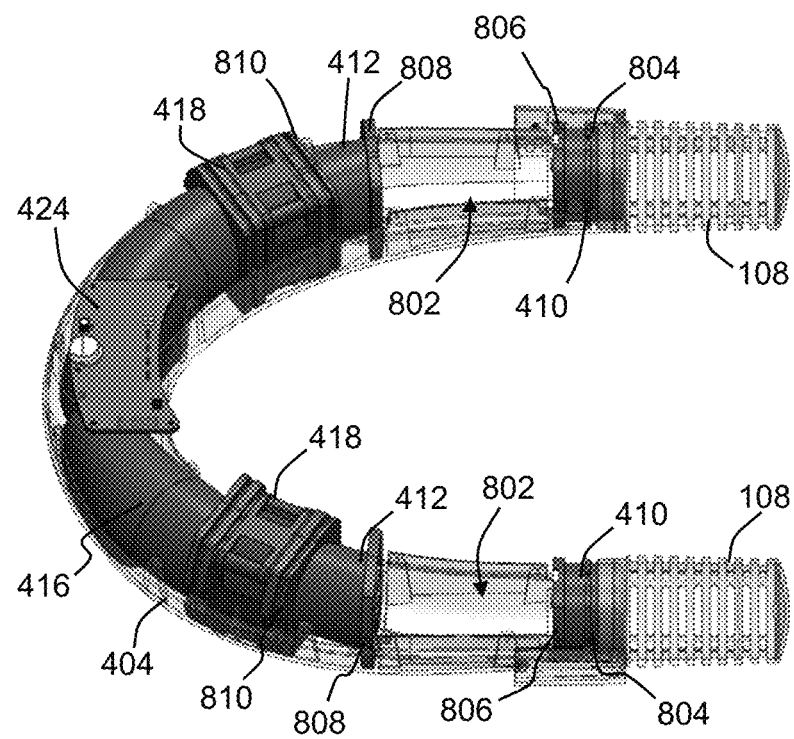
FIG. 8 representatively illustrates a housing with an upper cover removed to show internal components in accordance with an exemplary embodiment of the present technology.
Figure 9:
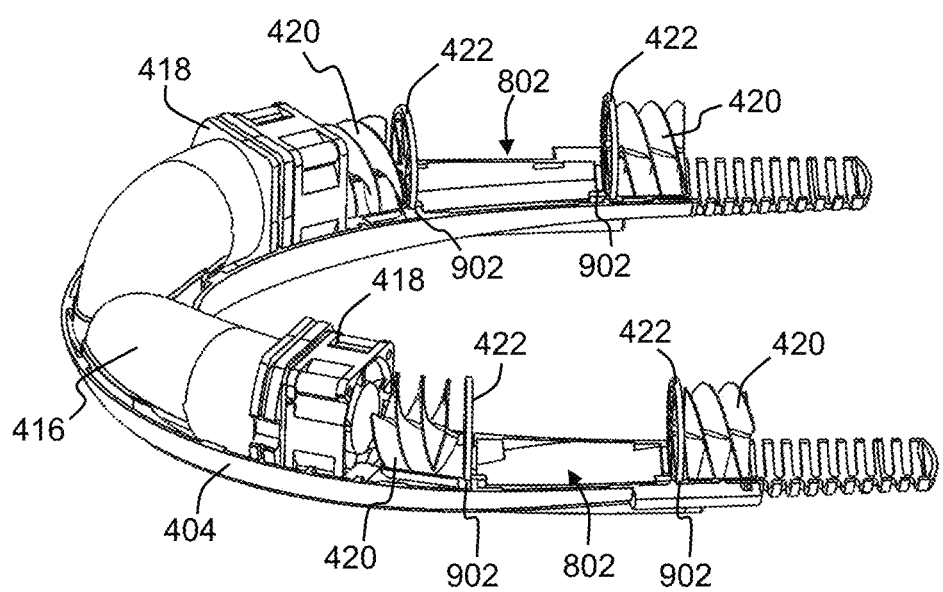
FIG. 9 representatively illustrates a housing with an upper cover and portions of the air duct removed to show internal components in accordance with an exemplary embodiment of the present technology.

In one embodiment, the air sterilization system 414 may comprise a UV light sterilization system installed on each side of the duct and be configured to use UV light to kill bacteria and viral particulates in the airflow coming from the air filtration system 108. For example, the UV light sterilization system may comprise a pair of UV light emitters 422 and a pair of light shields 420. With particular reference to FIGS. 8 and 9, one emitter 422 and one light shield 420 may be located at opposite ends of a UV sterilization chamber 802.

In an alternative embodiment, the UV light sterilization system may be positioned along the wall of the UV sterilization chamber 802. For example, a series of UV light emitters 422 may be arranged along the length of the UV sterilization chamber 802 to ensure UV exposure along the entirety of the UV sterilization chamber 802.

The UV sterilization chamber 802 provides an air path between the two emitters 422 configured to generate or support vortex (turbulent) air movement within the UV sterilization chamber 802 to increase the residence time of molecules in the UV sterilization chamber 802. Longer residence time within the UV sterilization chamber 802 and turbulent flow increase the exposure dose to fly-by molecules and encourages a more uniform particle exposure during the residency time. More specifically, as molecules within the mass flow rate of air rotate in the flow and pass between the two ends of the UV sterilization chamber 802, they get exposed to UV light from different sides and angles. Multi-angle exposure has been shown to be more effective for inactivation of viruses and bacteria. For example, exposure dose to deactivate viruses is typically lower in air than on a solid surface because the molecules in air are exposed to UV light from multiple directions simultaneously. Thus, particles get higher exposure dose without a need to increase the power or intensity of the UV light itself.

The UV sterilization chamber 802 may also be configured to shield the user from visual exposure to UV light from the UV light emitters 422. For example, the UV sterilization chamber 802 may comprise an opaque chamber housing, cover, or duct that allows the airflow to pass without providing a direct pathway for light to exit the UV sterilization chamber 802. In one embodiment, the UV sterilization chamber 802 may comprise an inner geometry configured to block the escape of UV light from within the UV sterilization chamber 802. Because no light can escape the UV sterilization chamber 802, user exposure to UV light is reduced or completely eliminated.

To further increase the UV sterilization efficiency surfaces of the walls of the UV sterilization chamber 802 may be coated with light blocking coating and sheathed with an aluminum foil. Other UV blocking and reflective surfaces may be used to help improve efficacy of the UV sterilization chamber 802. For example, sintered PTFE sheets may be cut to a specific shape to line the walls of the UV sterilization chamber 802.

The light shields 420 may also be used to prevent UV light from escaping the UV sterilization chamber 802. The light shields 420 may also be configured to provide an air path having a more turbulent airflow to increase the residency time and exposure of molecules within the airflow of the UV sterilization chamber 802. This may be achieved with various geometrical shapes, with consideration given to the dual purpose of blocking light escape and impacting airflow in a desired manner.

Figure 10:
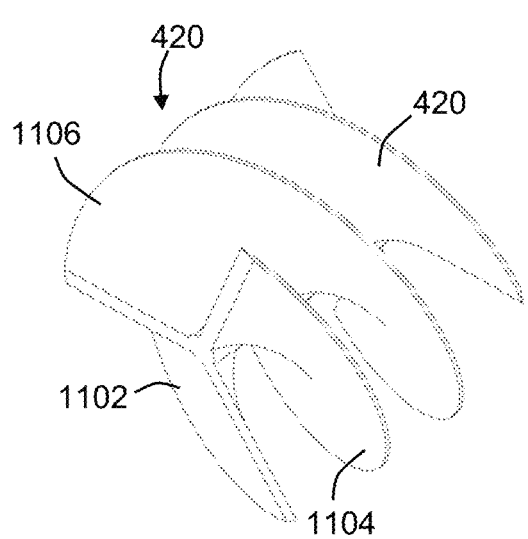
FIG. 10 representatively illustrates a perspective view of a light shield in accordance with an exemplary embodiment of the present technology.
Figure 11:
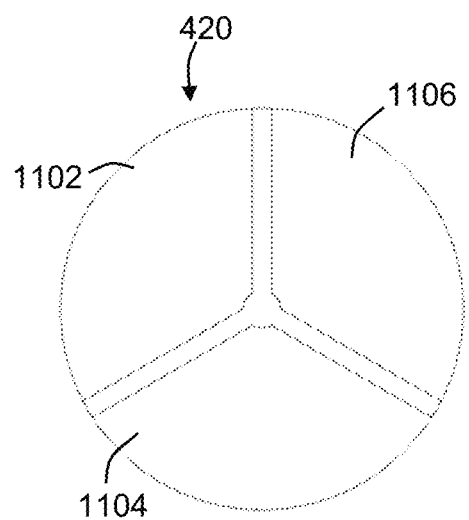
FIG. 11 representatively illustrates an end view of the light shield in accordance with an exemplary embodiment of the present technology.

Referring now to FIGS. 9-11, in one embodiment, each light shield 420 may comprise a light curtain having three intertwined surfaces 1102, 1104, 1106 that extend along the length of the light curtain. The surfaces may be intertwined to prevent direct UV light from propagating through the light shield 420. For example, the intertwined surfaces 1102, 1104, 1106 may comprise a pattern of concave intrusions that are off-set with respect to each other in such a way that prevents propagation of light beams due to off-surface reflection. Alternatively, an irregular homogeneous surface roughness to each intertwined surface 1102, 1104, 1106 may have a similar light entrapping effect. The attenuation of light may be further suppressed by coating the surface of the light shield 420 with non-reflective material.

The intertwined arrangement of light blocking geometries may also increase the exposure dose received in UV sterilization chamber 802. For example, the geometry of intertwined surfaces 1102, 1104, 1106 may help create a vortex flow of air as it enters the UV sterilization chamber 802 as a result of the incoming airflow having to flow along entire length of the screw-like pattern of the intertwined surfaces 1102, 1104, 1106. Air flowing past the first light shield 420 at an inlet side of the UV sterilization chamber 802 may impart a rotary motion to the airflow as it passes creating a vortex flow pattern as the airflow enters the UV sterilization chamber 802. Due to created turbulence, the particles are rotated and exposed from multiple angles as described above.

Figure 16:
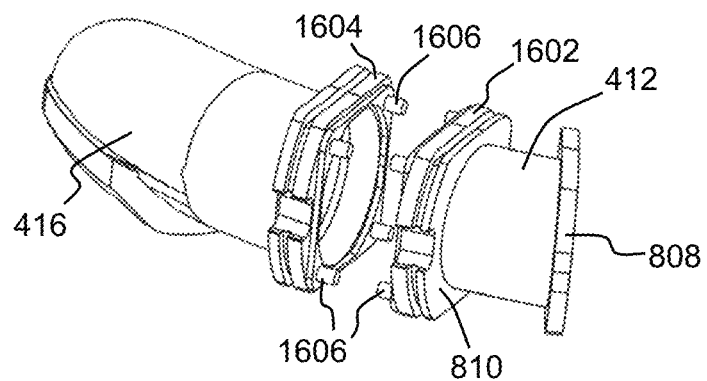
FIG. 16 representatively illustrates a close up view of an air fan mounting system in accordance with an exemplary embodiment of the present technology.
Figure 17:
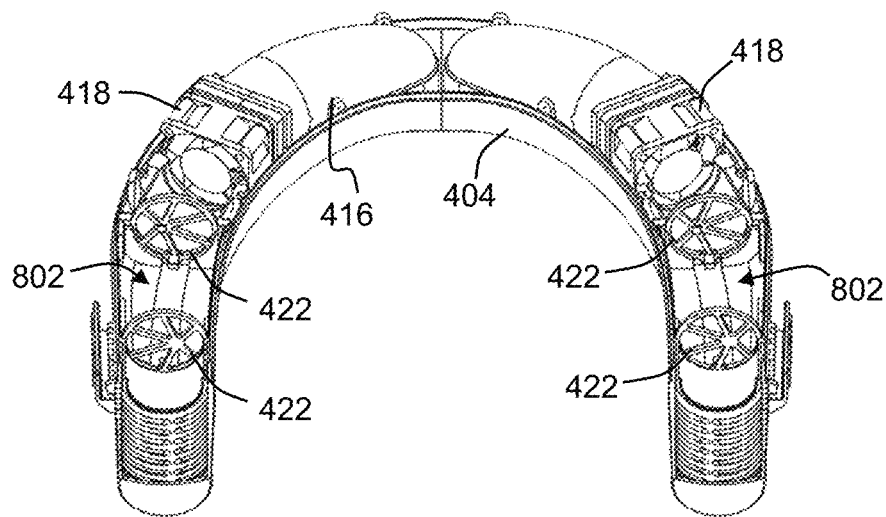
FIG. 17 representatively illustrates a rear view of the internal ducting and UV light chamber in accordance with an exemplary embodiment of the present technology.
Figure 18:
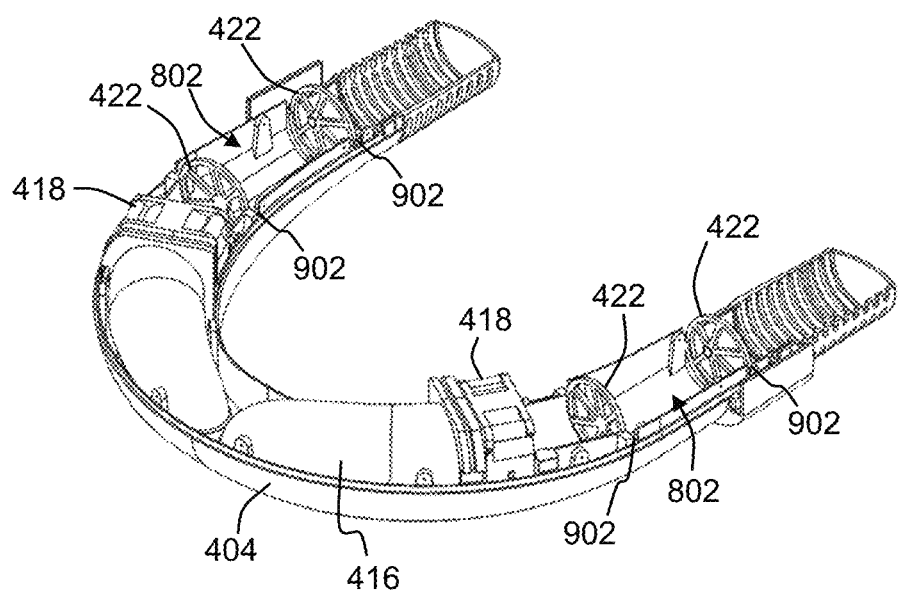
FIG. 18 representatively illustrates a forward perspective view of the internal ducting and UV light chamber in accordance with an exemplary embodiment of the present technology.
Figure 19:
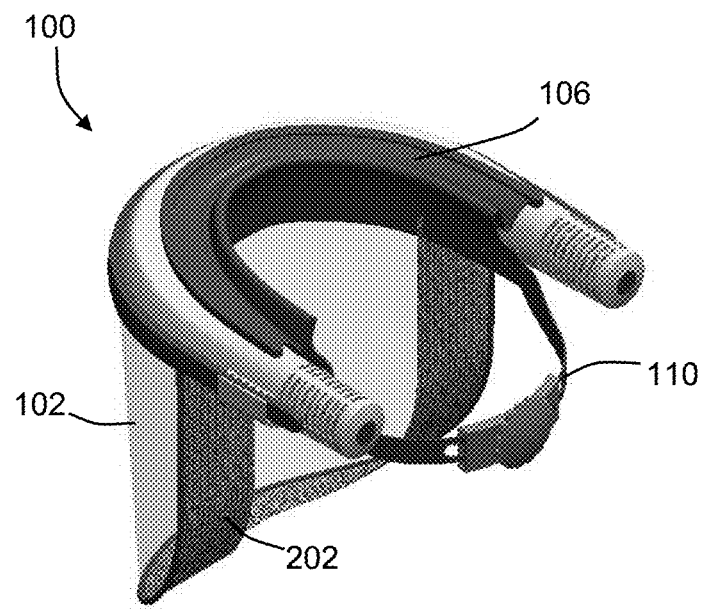
FIG. 19 representatively illustrates a detailed view of an edge shield in accordance with an exemplary embodiment of the present technology.

Referring again to FIGS. 9, 16, and 17, in one embodiment, a UV light emitter 422 may be positioned at each end of the UV sterilization chamber 802. In alternative embodiments, there may be more or fewer UV light emitters used. For example, in some embodiments, a single UV light emitter 422 may be used. In other embodiments, three or more light emitters 422 may be arranged around or within the UV sterilization chamber 802 to treat the passing airflow.

The UV light emitter 422 may comprise any suitable UV light source 1206 having a wavelength and output power sufficient to kill or otherwise destroy a desired range of bacteria and viruses. For example, in one embodiment, the UV light source 1206 may comprise one or more light emitting diodes (LED) configured to provide a UV light within the C band spectrum or between about 200 nm and about 280 nm. In an alternative embodiment, the UV light source 1206 may comprise one or more UV bulbs that also cover the C band of the UV spectrum. The UV light source 1206 may also be selected according to a desired or available power source such as an onboard or remote battery system. Power or intensity of each emitter 422 may be adjusted by any suitable method such as increasing either the power of each UV light source 1206 or increasing the number of UV light sources 1206 on each light emitter 422.

Figure 12:
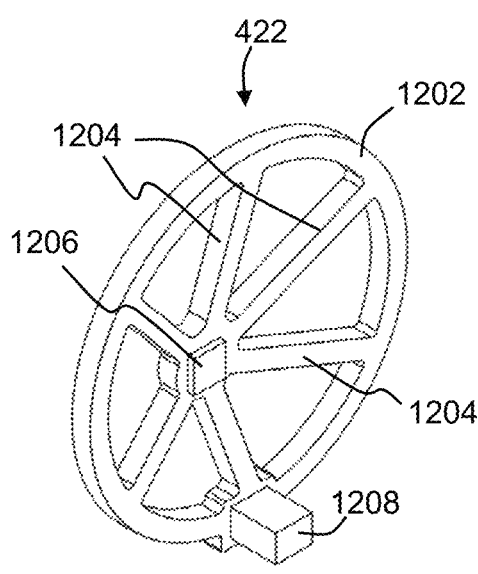
FIG. 12 representatively illustrates a perspective view of an ultraviolet light emitter in accordance with an exemplary embodiment of the present technology.
Figure 13:
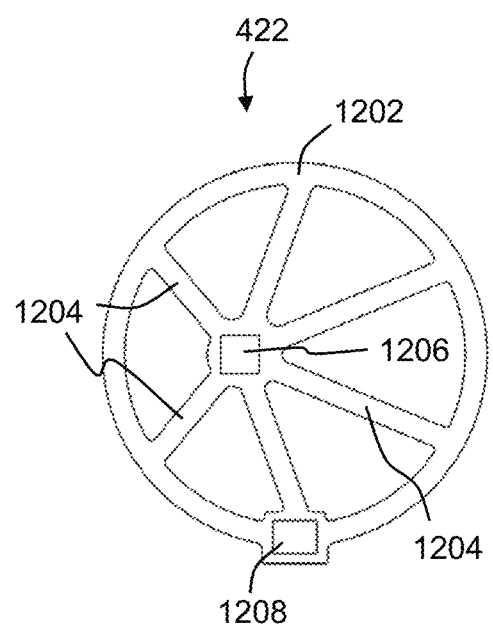
FIG. 13 representatively illustrates an end view of the ultraviolet light emitter in accordance with an exemplary embodiment of the present technology.
Figure 14:
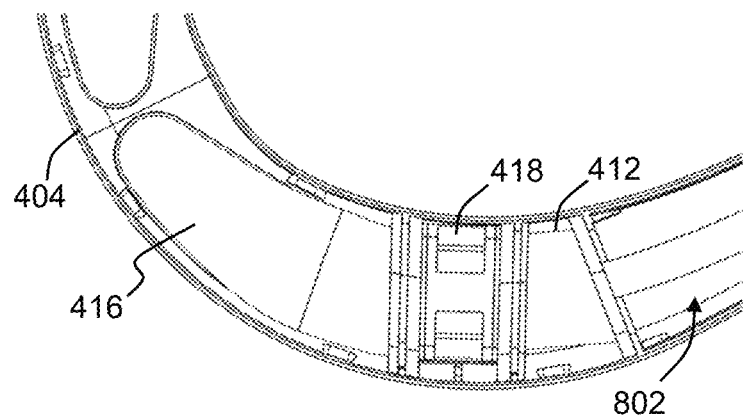
FIG. 14 representatively illustrates a close up view of internal ducting in accordance with an exemplary embodiment of the present technology.
Figure 15:
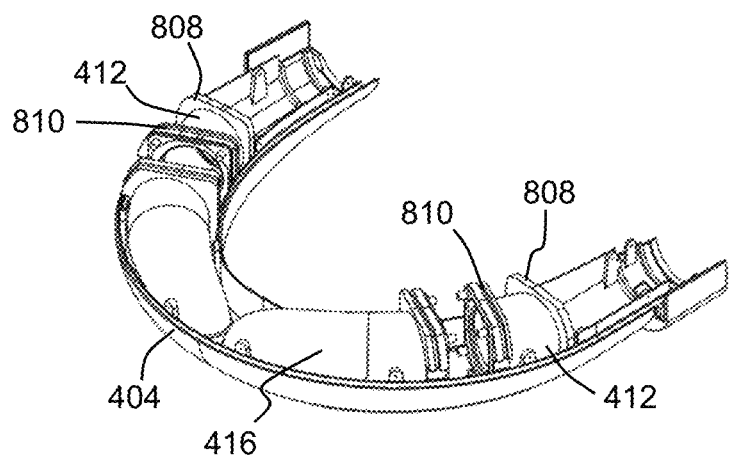
FIG. 15 representatively illustrates a perspective view of the internal ducting with the air fans removed in accordance with an exemplary embodiment of the present technology.

Referring now to FIGS. 12, and 13, each UV light emitter 422 may be installed on a separate electronics board or frame 1202 which may be inserted into a receiving notch 902 in the lower cover 404 of the housing 104. The frame 1202 may comprise any suitable size or shape configured to allow the UV light source 1206 to project light into the UV sterilization chamber 802 while also allowing air to flow past the frame.

In one embodiment, the frame 1202 may comprise a circular body having a diameter substantially the same as a diameter of the dual-sided duct. The frame 1202 may comprise a set of spokes 1204 extending inwardly from to an outer peripheral edge of the frame 1202 towards a central junction point. The UV light source 1206 may be located at the junction point of the set of spokes 1204. In one embodiment, the junction point may be located at the center axis of the circular body such that each spoke 1204 has the same length.

In a second embodiment, the junction point of the spokes 1204 may be shifted off the center axis such that one or more of the spokes 1204 may not have the same length. For example, as shown in FIGS. 12 and 13, the junction point may be shifted from the center axis towards one side of the frame 1202 causing some spokes 1204 to have shorter lengths than other spokes 1204. As a result, the UV light source 1206 of each UV light emitter 422 may be shifted from the central axis with respect to each other to increase the area of high intensity. This results in a higher exposure limit, intensity, and accounts for an output distribution of each UV light emitter 422 that covers a general parabolic area with respect to UV light source 1206.

To avoid the situation of two UV light sources 1206 shining straight into each other and creating a first zone with more light intensity and one or more additional zones with less light intensity, shifting the junction point off axis and rotating the emitter 422 located at the inlet side with respect to the UV light emitter 422 located at the outlet side of the UVC sterilization chamber 802 may create a more uniform distribution of UV light throughout the UV sterilization chamber 802. For example, the UV light emitter 422 at the outlet side of the UV sterilization chamber 802 may be rotated relative to the UV light emitter 422 at the inlet side by an angle of between about 45 degrees and about 180 degrees. This rotation may create a more uniform distribution of UV light throughout the entire UV sterilization chamber 802.

Varying the location of the junction point on the frame 1202 may be used to create a more intense region of UV light in a given section of the UV sterilization chamber 802. For example, the amount that the junction point is moved away from the center axis of the frame 1202 may shift a region of highest light intensity nearer the walls of the UV sterilization chamber 802 and away from the center of the UV sterilization chamber 802. Such an arrangement may be desirable to account for an increased amount of the airflow along the walls of the UV sterilization chamber 802 and a lower more static regions of air closer to the center axis of the UV sterilization chamber 802 resulting from the vortex nature of the airflow itself. Because air located closer to the central axis of the UV sterilization chamber 802 may progress through the UV sterilization chamber 802 at a slower rate the air may have a longer exposure time. The longer exposure time may allow for a lower intensity level of UV light exposure in contrast to the airflow along the walls of the UV sterilization chamber 802 which have a shorter exposure time and require a higher intensity level of UV light to achieve the desired level of sterilization.

The frame 1202 may comprise a printed circuit board having an aluminum or other metallic core. A metallic core of the board may provide structural support for the UV light source 1206 during use and the core may further act as a heatsink to dissipate thermal energy created by the UV light source 1206 during operation. The spokes 1204 of the frame may further increase heat dissipation capacity wherein each spoke 1204 acts as a thermal fin dissipating heat from the frame 1202 into the passing airflow.

The frame 1202 may also comprise one or more sensor devices (not shown) for detecting desired conditions or environmental factors. For example, the frame 1202 may comprise a temperature sensing device to monitor the temperature of the UV light source 1206 during operation. Alternatively, or in addition to, the frame may also comprise a sensor configured to monitor airflow past the UV light emitter 422. Data collected from the sensors may be communicated to the electronic control system 424 through an electrical connector 1208. The electrical connector 1208 may comprise any suitable connector or device for providing power and data communication between the UV light emitter 422 and the electronic control system 424.

Referring again to FIGS. 4 and 8, the duct system helps direct and control the mass flow of air through the personal protective respiratory device 100. In one embodiment, each side of the duct system may comprise a first light shield duct 410 and a second light shield duct 412. Passing airflow from both sides may meet at an exhaust duct 416. A first end 804 of the first light shield duct 410 may be coupled to an outlet side of the air filtration system 108 and be configured to receive the filtered air and direct the flow across the first light shield 420. A second end 806 of the first light shield duct 410 may be coupled to the inlet side of the UV sterilization chamber 802. The second end 806 may also be configured to house or at least partially cover the first UV light emitter 422.

Referring now to FIGS. 8 and 14-16, a first end 808 of the second light shield duct 412 may be coupled to an outlet side of the UV sterilization chamber 802 and be configured to receive the filtered and sterilized air and direct the flow across the second light shield 420. A second end 810 of the second light shield duct 412 may be coupled to the inlet side of the air fan 418. The first end 810 of the second light shield duct 412 may also be configured to house or at least partially cover the second UV light emitter 422.

With reference to FIGS. 8 and 14-18, the exhaust duct 416 may be located downstream of and connected to an outlet side of the air fan 418 and be configured to direct the purified airflow onto the face shield 104. The exhaust duct 416 may comprise any suitable device for allowing air to exit the housing 104. For example, in one embodiment, the exhaust duct 416 may comprise a series of openings or holes in the housing 104. In another embodiment, the exhaust duct 416 may comprise a series of nozzles configured to direct portions of the exiting airflow onto specific areas of the face shield 102. In yet another embodiment, the exhaust duct 416 may comprise the set of air outlets 204.

The set of air outlets 204 are configured to supply filtered and sterilized air at a flow rate to the proximity of the nose and mouth area under face shield 102 to create a positive air pressure region under the face shield 102 to prevent inward entrance of particles towards the user's face. The set of air outlets 204 are configured to direct the airflow in the face-visor region downwards to the nose and mouth area avoiding eye areas. Directing airflow downward may help prevent drying of the user's eyes during use and the flow may help drive exhaled breath downwardly away from the user's eyes helping prevent fogging of the face shield 102.

The duct system may also be configured to reduce vibrations generated by the air fans 418. Any suitable system or method may be used to reduce or otherwise limit the amount of vibrational energy transferred from the air fans 418 to the duct system or the housing 104. In one embodiment, the second light shield duct 412 and the exhaust duct 416 may comprise a fan mounting system configured to decouple the air fans 418 from direct contact with any solid portion of the housing 104. For example, and referring now to FIG. 16, the fan mounting system may suspend the air fans 418 in the housing 104 with a pair of vibration damping brackets 1602, 1604. The second light shield duct 412 and the exhaust duct 416 may comprise a soft material configured to attenuate vibration propagation. Each vibration damping bracket 1602, 1604 may comprise a set of four pins 1606 on its contact surface that engage the air fan 418. The eight pins 1606 may be inserted into a housing body of the air fan 418 and support the air fan 418 in place between the second light shield duct 412 and the exhaust duct 416. The vibration damping brackets 1602, 1604 may act as a vibration cancelling or isolation system by effectively decoupling the air fans 418 from the housing 104. Damping efficiency of the vibration damping brackets 1602, 1604 may be determined by properties of the materials used to form the second light shield duct 412 and the exhaust duct 416. For example, the softness, thickness, and flexibility of the vibration damping brackets 1602, 1604 helps determine an amount of vibrational dampening.

The second light shield duct 412 and the exhaust duct 416 may each comprise any suitable material or combination of materials to provide a desired level of vibration damping or isolation. For example, the second light shield duct 412 and the exhaust duct 416 may comprise a combination of polymer materials with each having a distinct vibration isolating range such that the amount of vibration damping provided may change in accordance with a change in speed of the air fans 418 or any mechanical issues such as a fan imbalance.

Referring again to FIGS. 1-4, the face shield 102 extends downwardly from the housing 104 to cover the user's face during use and provides a physical barrier that protects the user's eyes from direct contact with the particles and microdroplets in the ambient air or from hand-face touch. The face shield 102 may generally conform to or follow the curvature of the housing 104 to provide a wrap-around fit and increased protection to the user from airborne particulates striking the face of the user.

The face shield 102 also helps direct the airflow exiting the housing 104 in manner to reduce the likelihood that ambient air can enter into the region between the face shield 102 and the user's face. More specifically, the airflow exiting the housing 104 is generally directed downward and around the user's face by the face shield 102. This creates a pressurize region in the region between the face shield 102 and the user's face compared to the ambient environment. This elevated-pressure region acts to prevent ambient air from entering the region between the face shield 102 and the user's face, providing increased protection for the user from airborne viruses, bacteria, chemicals, or other particulate matter in the ambient air. Exhaled air is removed from the proximity of nose and mouth area by airflow under the face shield 102. Thus, no immediate recirculation of exhaled breath gas can occur.

The face shield 102 may comprise an edge filter 202 configured to capture exhaled microdroplets on its surface to prevent their spread. With particular reference to FIGS. 2C, 2D, 3D, 4, and 19, the edge filter 202 may comprise any suitable device or filtering membrane configured to capture and generally prevent microdroplets from becoming airborne after capture. In one embodiment, the edge filter 202 may comprise a textile filter disposed along an outer edge the face shield 102. The face shield 102 may comprise a shape modeled to act as an air-foil to direct exhaled microdroplets onto the edge filter 202

The face shield 102 may be connected to the housing 104 by any suitable device or method. For example, the face shield 102 may be attached to the housing 104 with a flexible linear bracket 430. The bracket 430 may be made of flexible material that can be extended and put in tension to clamp the face shield 102 between the bracket 430 and the housing 104. The bracket 430 and the housing 104 may have a corresponding male-female geometry that are engaged through a set of holes 432 in the face shield 102 that fit around a set of protrusions 434 in the housing 104. The bracket 430 may also comprise a set of teeth configured to engage a mating set of ridges on a surface of the housing 104 that are configured to adjust the tension between the face shield 102 and the housing 104.

Figure 20:
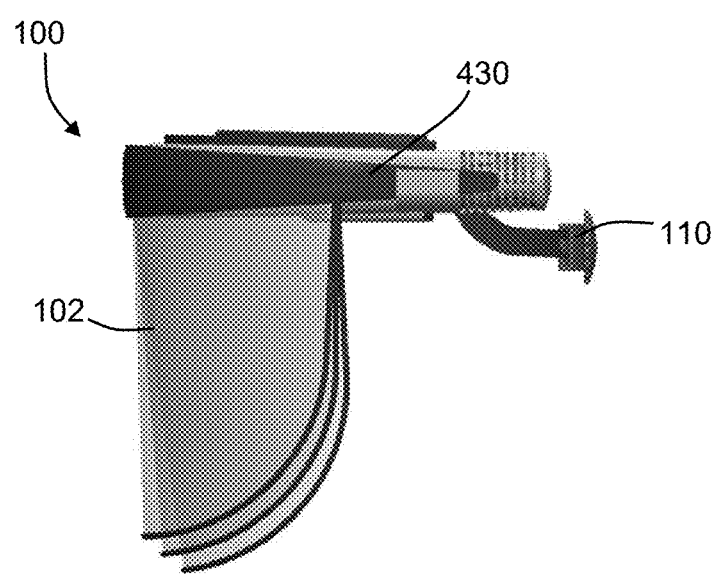
FIG. 20 representatively illustrates a rotary movement of the face shield and bracket relative to the housing in accordance with an exemplary embodiment of the present technology.

Referring now to FIG. 20, the bracket 430 may also be configured to allow an angle of the face shield 102 to be altered with respect to the housing 104 for the user's comfort. For example, the bracket 430 may comprise a tilt mechanism that allows the face shield to be rotated relative to the housing 104. In one embodiment, the bracket 430 is made of a soft and flexible material that allows small rotary motion of the bracket 430 and face shield 102 due to material defection of about +/−5 degrees relative to the housing 104.

Referring now to FIGS. 4 and 8, the electronic control system 424 controls operation of the personal protective respiratory device 100 and may be configured to monitor, control, or adjust any function of the personal protective respiratory device 100. For example, the electronic control system 424 may be configured to control the speed of the air fans 418 fans and adjust the power of emitters 422.

As described above, the frame 1202 of each UV light emitter 422 may be equipped with temperature sensors to monitor the temperature of the UV light source 1206. If the electronic control system 424 detects an unsafe temperature level, the electronic control system 424 may generate a signal or otherwise notify a user and automatically power the system down. Similarly, the electronic control system 424 may be configured to monitor the speed of each air fan 418. If the electronic control system 424 detects the failure of one or more of the air fans 418, then the UV light emitter 422 that is in the same airflow path as the failed air fan 418, or both sets of UV light emitters 422, may be powered down to avoid overheating. The remaining air fan 418 may be kept working to provide filtered air to a user. The electronic control system 424 may also generate a signal to the user to notify them of the detected condition.

The electronic control system 424 may also be configured to monitor general performance of the personal protective respiratory device 100. For example, the electronic control system 424 may track the number of operated hours and generate a signal to inform a user to change the filtration media after a specified number of operational hours have passed. The electronic control system 424 may also be configured to control a personal communication system having a microphone and speakers that transmit a signal to a local receptor/transceiver device such as a wireless connection to a cell phone or other computing device.

The electronic control system 424 may be powered by any suitable method. In one embodiment, an external battery may be connected to the housing 104 through a wired connection. In an alternative embodiment, an onboard power supply may be used to power the electronic control system 424 and the air fans 418.

Figure 21:
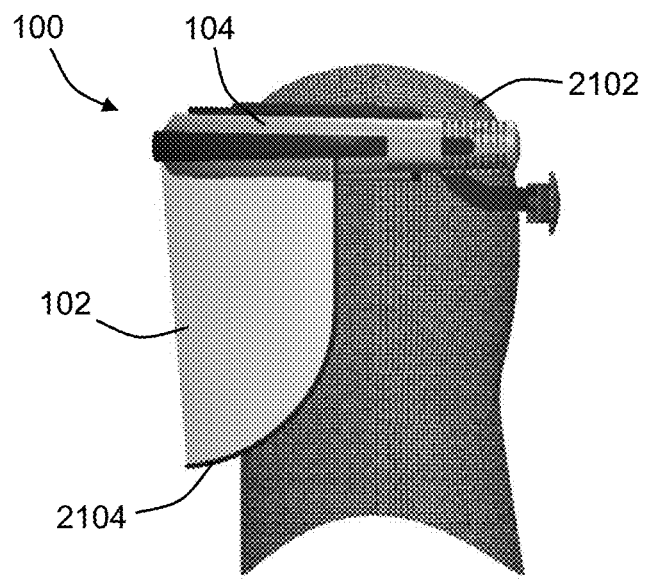
FIG. 21 representatively illustrates a side view of an alternative embodiment of the personal respiratory device incorporating a head gown in accordance with an exemplary embodiment of the present technology.
Figure 22:
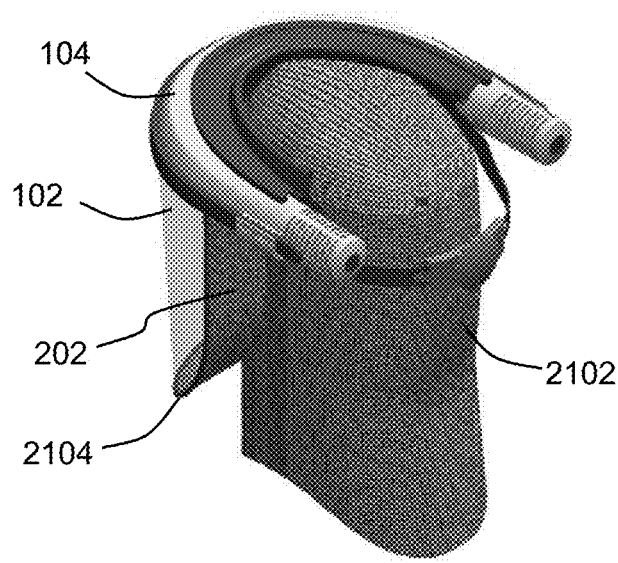
FIG. 22 representatively illustrates a rear perspective view of the personal respiratory device shown in FIG. 21 in accordance with an exemplary embodiment of the present technology.

Referring now to FIGS. 21 and 22, the personal protective respiratory device 100 may further be configured to include a head gown 2102 configured to provide an airtight sealed enclosure to the face shield 102 in which only filtered and sterilized air is supplied. The head gown 2102 may comprise any system or device for reducing a potential for respiratory droplets, secretions, or other respiratory particulates from migrating outward from the sealed regions of the personal protective respiratory device 100 to the surrounding ambient environment. Similarly, the head gown 2102 will act to prevent respiratory particulates in the ambient environment from entering into the sealed region of the personal protective respiratory device 100.

In one embodiment, the head gown may comprise an upper hood portion to at least partially cover the user's head and a lower hood portion configured create barrier that prevents the movement of particulates between the ambient environment and the elevated pressure region between the face shield 102 and the user's face.

A positive pressure inside the head gown 2102 establishes the outflow of exhaled breath. For example, the head gown 2102 may comprise a breathable material configured to allow exhaled air and excess airflow from the housing 104 to exit into the ambient environment while trapping droplets and other particulates. The breathable material may comprise any suitable fabric, textile, paper, or other material capable of capturing respiratory droplets but otherwise permeable to air. The breathable material may comprise a single use medical grade material or it may comprise a material that can be cleaned, sterilized, and reused. The breathable material may also comprise openings with a filtering material to filter exhaled breath as it passes through the head gown 2102.

In one embodiment, the head gown 2102 may comprise a textile-like membrane. The head gown 2102 may also allow for a decrease in airflow through the personal protective respiratory device 100 due to smaller rate of outflow of airflow to the ambient environment. The head gown 2102 may create a small positive pressure inside the hood and any airborne particles captured on the head gown 2102 may be forced to diffuse away through the surface due to small outward airflow through the head gown 2102 material.

Figure 23:
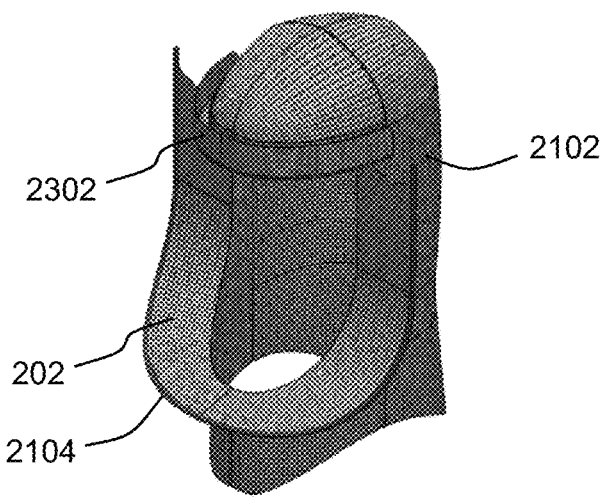
FIG. 23 representatively illustrates the head gown in accordance with an exemplary embodiment of the present technology.
Figure 24:
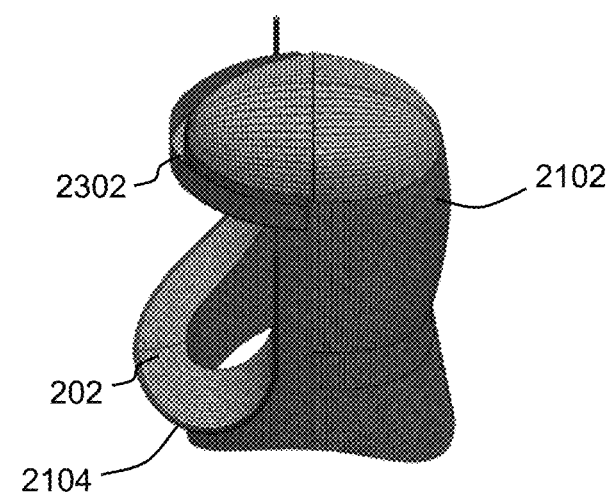
FIG. 24 representatively illustrates a side view of the head gown in accordance with an exemplary embodiment of the present technology.

Referring now to FIGS. 23 and 24, the head gown 2102 may comprise a U-shaped flap 2302 in an upper front portion. The flap 2302 may be configured to engage the housing 104 to be secured in place. For example, the flap 2302 may be inserted under the head cushion 106 and squeezed between the housing 104 and the head cushion 106. The flap 2302 of the head gown 2102 helps ensure an airtight seal.

With continued reference to FIGS. 21-24, the head gown 2102 may also be integrated with the edge filter 202 to provide a complete seal. Alternatively, the head gown 1902 may be configured to be coupled to the edge filter 202 to create a seal. In one embodiment, the head gown 2102 includes a portion that extends forward and connects with an edge of the face shield 102. For example, a plastic clamp 2104 may be used to fasten the head gown 2102 to the edge of the face shield 102. In an alternative embodiment, the clamp 2104 may be substituted with a zipper when the head gown 2102 is made of material for multiple uses. In yet another embodiment, the clamp 2104 may be substituted with an adhesive at the edge of the disposable head gown 2102 configured to couple the head gown 2102 to the face shield 102 and housing 104.

These and other embodiments for a personal protective respiratory device 100 may incorporate concepts, embodiments, and configurations as described above. The particular implementations shown and described are illustrative of the technology and its best mode and are not intended to otherwise limit the scope of the present technology in any way. Indeed, for the sake of brevity, conventional manufacturing, connection, preparation, and other functional aspects of the system may not be described in detail. Furthermore, the connecting lines shown in the various figures are intended to represent exemplary functional relationships and/or physical couplings between the various elements. Many alternative or additional functional relationships or physical connections may be present in a practical system.

The description and figures are to be regarded in an illustrative manner, rather than a restrictive one and all such modifications are intended to be included within the scope of the present technology. Accordingly, the scope of the technology should be determined by the generic embodiments described and their legal equivalents rather than by merely the specific examples described above. For example, the components and/or elements recited in any apparatus embodiment may be assembled or otherwise operationally configured in a variety of permutations to produce substantially the same result as the present technology and are accordingly not limited to the specific configuration recited in the specific examples.

As used herein, the terms "comprises," "comprising," or any variation thereof, are intended to reference a non-exclusive inclusion, such that a process, method, article, composition or apparatus that comprises a list of elements does not include only those elements recited, but may also include other elements not expressly listed or inherent to such process, method, article, composition or apparatus. Other combinations and/or modifications of the above-described structures, arrangements, applications, proportions, elements, materials or components used in the practice of the present technology, in addition to those not specifically recited, may be varied or otherwise particularly adapted to specific environments, manufacturing specifications, design parameters or other operating requirements without departing from the general principles of the same.

The present technology has been described above with reference to exemplary embodiments. However, changes and modifications may be made to the exemplary embodiments without departing from the scope of the present technology. These and other changes or modifications are intended to be included within the scope of the present technology, as expressed in the following claims.

The invention claimed is:

1. A personal protective respiratory device, comprising:
a housing having an interior volume, comprising:
   a curved center section;
   two opposing side sections, wherein:
      a first side section extends away from a first side of the curved center section to a first inlet; and
      a second side section extends away from a second side of the curved center section to a second inlet, wherein an open space separates the second side section from the first side section;
an air duct system disposed within the interior volume, wherein:
   a first duct section is located in the first side section;
   a second duct section is located in the second side section; and
   an exhaust duct is located in the curved center section and comprises a set of air outlets configured to receive an airflow from the first and second duct sections;
an air filtration system, comprising:
   a first filtration element disposed at the first inlet; and
   a second filtration element disposed at the second inlet;
an air sterilization system, comprising:
   a first UV light sterilization system disposed downstream of the first filtration element; and
   a second UV light sterilization system disposed downstream of the second filtration element; and
a pair of air fans, wherein:
   a first air fan is positioned in the first side section and configured to generate a first mass flow of air between the first inlet and the exhaust duct; and
   a second air fan is positioned in the second side section and configured to generate a second mass flow of air between the second inlet and the exhaust duct;
a head cushion coupled to the housing; and
a face shield extending downwardly from the curved center section and at least a portion of the first and second side sections of the housing.

2. A personal protective respiratory device according to claim 1, wherein:
the first air fan is positioned between the first UV light sterilization system and the exhaust duct; and
the second air fan is positioned between the second UV light sterilization system and the exhaust duct.

3. A personal protective respiratory device according to claim 1, wherein the first and second UV light sterilization system each comprise:
a sterilization chamber;
a pair of UV light emitters; and
a pair of light shields.

4. A personal protective respiratory device according to claim 3, wherein:
a first light shield is located at an inlet side of each sterilization chamber;
a second light shield is located at an outlet side of each sterilization chamber;
a first UV light emitter is positioned between each sterilization chamber and the first light shield; and
a second UV light emitter is positioned between each sterilization chamber and the second light shield.

5. A personal protective respiratory device according to claim 4, wherein first and second duct sections each comprise:
a first light shield duct housing each first light shield; and
a second light shield duct housing each second light shield.

6. A personal protective respiratory device according to claim 4, wherein each first light shield comprises three intertwined surfaces extending along a length of each first light shield, wherein the three intertwined surfaces form a geometry configured to generate a vortex flow of air into each sterilization chamber.

7. A personal protective respiratory device according to claim 4, wherein each UV light emitter comprises:
a circular frame;
a set of spokes extending inwardly from an outer periphery of the circular frame to a junction point located within a perimeter of the circular frame; and
a UV light source positioned on the junction point.

8. A personal protective respiratory device according to claim 7, wherein each junction point is offset from a center axis of the circular frame.

9. A personal protective respiratory device according to claim 8, wherein each of the first and second UV light emitters are rotated between forty-five and one hundred eighty degrees relative to each other.

10. A personal protective respiratory device according to claim 1, wherein the head cushion comprises:
a flexible head strap having a curved center section and two opposing side sections; and
an adjustment mechanism extending between the two opposing side sections.

11. A personal protective respiratory device according to claim 10, wherein the flexible head strap comprises a double bend profile configured to absorb vibrational energy from the housing.

12. A personal protective respiratory device according to claim 1, the duct system further comprises a vibration damping system connected to each air fan.

13. A personal protective respiratory device according to claim 1, wherein the face shield further comprises a textile filter disposed along an outer edge the face shield.

14. A personal protective respiratory device according to claim 1, wherein the face shield further comprises a head gown comprising an air permeable breathable material capable of capturing respiratory droplets.

15. A personal protective respiratory device, comprising:
a housing having an interior volume and comprising:
an inlet located at a rear of the housing;
an exhaust duct located in a forward section of the housing; and
a duct system extending between the inlet and the exhaust duct;
an air filtration system, comprising a filtration element disposed at first inlet;
an air sterilization system, comprising a UV light sterilization system disposed downstream of the filtration element;
an air fan positioned downstream of the UV light sterilization system and configured to generate a mass flow of air between the inlet and the exhaust duct;
a head cushion coupled to the housing; and
a face shield extending downwardly from the housing.

16. A personal protective respiratory device according to claim 15, wherein the UV light sterilization system comprises:
a sterilization chamber;
a pair of UV light emitters; and
a pair of light shields.

17. A personal protective respiratory device according to claim 16, wherein:
a first light shield is located at an inlet side of the sterilization chamber;
a second light shield is located at an outlet side of the sterilization chamber;
a first UV light emitter is positioned between the sterilization chamber and the first light shield; and
a second UV light emitter is positioned between the sterilization chamber and the second light shield.

18. A personal protective respiratory device according to claim 17, wherein the first light shield comprises three intertwined surfaces extending along a length of each light shield, wherein the three intertwined surfaces form a geometry configured to generate a vortex flow of air into the sterilization chamber.

19. A personal protective respiratory device according to claim 16, wherein each UV light emitter comprises:
a circular frame;
a set of spokes extending inwardly from an outer periphery of the circular frame to a junction point located within a perimeter of the circular frame, wherein the junction point is offset from a center axis of the circular frame; and
a UV light source positioned on the junction point.

20. A personal protective respiratory device according to claim 15, wherein the head cushion comprises:
a flexible head strap comprising a double bend profile configured to absorb vibrational energy from the housing; and
an adjustment mechanism extending between the two opposing side sections of the head cushion.

21. A personal protective respiratory device according to claim 15, further comprising a vibration damping system connected to the air fan.

22. A personal protective respiratory device according to claim 15, wherein the face shield further comprises a textile filter disposed along an outer edge the face shield.

23. A personal protective respiratory device according to claim 15, further comprising a head gown coupled to the housing and the face shield, wherein the head gown comprises an air permeable breathable material capable of capturing respiratory droplets.

24. A personal protective respiratory device for use around a user's head, comprising:
a housing having an interior volume formed by a curved center section and two opposing side sections, comprising:
a first inlet end located in a first side section;
a second inlet end located in a second side section;
an exhaust duct located in the curved center section;
an air circulation system disposed within the interior volume of the housing between the first and second inlet ends and the exhaust duct and configured to generate a mass flow of air between the first and second inlet ends and the exhaust duct;
an air filtration system disposed within the interior volume of the housing proximate to the first and second inlet ends and configured to filter the mass flow of air; and
a UV light sterilization system disposed within the interior volume of the housing between the air filtration system and the exhaust duct and configured to sterilize the mass flow of air;
a head cushion coupled to the housing and configured to be positioned on the user's head; and
a face shield extending downwardly from the curved center section and at least a portion of the first and second side sections of the housing.

* * * * *